US00PP20971P2

(12) United States Plant Patent
Kientzler

(10) Patent No.: US PP20,971 P2
(45) Date of Patent: May 4, 2010

(54) **NEW GUINEA *IMPATIENS* PLANT NAMED 'VISINFSALIMP'**

(50) Latin Name: *Impatiens hawkeri*
Varietal Denomination: Visinfsalimp

(75) Inventor: Ludwig Kientzler, Gensingen (DE)

(73) Assignee: VisioPlant, Alajuela (CR)

( * ) Notice: Subject to any disclaimer, the term of this patent is extended or adjusted under 35 U.S.C. 154(b) by 0 days.

(21) Appl. No.: 12/321,349

(22) Filed: Jan. 16, 2009

(51) Int. Cl.
*A01H 5/00* (2006.01)

(52) U.S. Cl. ..... Plt./318.3

(58) Field of Classification Search ..... Plt./318.3
See application file for complete search history.

*Primary Examiner*—Kent L Bell
(74) *Attorney, Agent, or Firm*—C. A. Whealy

(57) ABSTRACT

A new and distinct cultivar of New Guinea *Impatiens* plant named 'Visinfsalimp', characterized by its compact, upright, outwardly spreading and mounded plant habit; freely branching habit; dense and bushy growth habit; vigorous growth habit; dark green-colored leaves; and numerous salmon-colored flowers that are positioned above and beyond the foliage.

1 Drawing Sheet

Botanical designation: *Impatiens hawkeri.*
Cultivar denomination: 'Visinfsalimp'.

BACKGROUND OF THE INVENTION

The present invention relates to a new and distinct cultivar of New Guinea *Impatiens* plant, botanically known as *Impatiens hawkeri*, and hereinafter referred to by the name 'Visinfsalimp'.

The new *Impatiens* plant is a product of a planned breeding program conducted by the Inventor in Gensingen, Germany. The objective of the breeding program was to develop new vigorous and freely branching *Impatiens* plants with numerous large flowers and attractive foliage and flower coloration.

The new *Impatiens* plant originated from a cross-pollination made by the Inventor in November, 2006, of a proprietary selection of *Impatiens hawkeri* identified as code No. 05-511, not patented, as the female, or seed, parent with *Impatiens hawkeri* 'Visinfsal', disclosed in U.S. Plant Pat. No. 16,275, as the male, or pollen, parent. The new *Impatiens* plant was discovered and selected by the Inventor as a flowering plant within the progeny of the stated cross-pollination in a controlled greenhouse environment in Gensingen, Germany in April, 2007.

Asexual reproduction of the new *Impatiens* plant by terminal cuttings propagated in a controlled greenhouse environment in Gensingen, Germany since May, 2007 has shown that the unique features of this new *Impatiens* plant are stable and reproduced true to type in successive generations of asexual reproduction.

SUMMARY OF THE INVENTION

Plants of the new *Impatiens* have not been observed under all possible environmental conditions. The phenotype may vary somewhat with variations in environment such as temperature and light intensity, without, however, any variance in genotype.

The following traits have been repeatedly observed and are determined to be the unique characteristics of 'Visinfsalimp'. These characteristics in combination distinguish 'Visinfsalimp' as a new and distinct cultivar of New Guinea *Impatiens*:

1. Compact, upright, outwardly spreading and mounded plant habit.
2. Freely branching habit; dense and bushy growth habit.

3. Vigorous growth habit.
4. Dark green-colored leaves.
5. Numerous salmon-colored flowers that are positioned above and beyond the foliage.

Plants of the new *Impatiens* differ primarily from plants of the female parent selection in the following characteristics:

1. Plants of the new *Impatiens* are more freely branching than plants of the female parent selection.
2. Plants of the new *Impatiens* have darker green-colored leaves than plants of the female parent selection.

Plants of the new *Impatiens* differ primarily from plants of the male parent, 'Visinfsal', in the following characteristics:

1. Plants of the new *Impatiens* are more freely branching than plants of 'Visinfsal'.
2. Plants of the new *Impatiens* have larger flowers than plants of 'Visinfsal'.
3. Flowers of plants of the new *Impatiens* are darker salmon in color than flowers of plants of 'Visinfsal'.

Plants of the new *Impatiens* can be compared to plants of New Guinea *Impatiens* 'Fisupnic Salmdeep', disclosed in U.S. Plant Pat. No. 17,755. In side-by-side comparisons conducted in Gensingen, Germany, plants of the new *Impatiens* differed primarily from plants of 'Fisupnic Salmdeep' in the following characteristics:

1. Plants of the new *Impatiens* were more compact than plants of 'Fisupnic Salmdeep'.
2. Plants of the new *Impatiens* and 'Fisupnic Salmdeep' differed in flower color.

BRIEF DESCRIPTION OF THE PHOTOGRAPHS

The accompanying photographs illustrate the overall appearance of the new *Impatiens* plant. The photographs show the colors as true as it is reasonably possible to obtain in colored reproductions of this type. Colors in the photographs may differ slightly from the color values cited in the detailed botanical description which accurately describe the colors of the new *Impatiens.*

The photograph at the bottom of the sheet comprises a side perspective view of a typical flowering plant of 'Visinfsalimp' grown in a container.

The photograph at the top of the sheet is a close-up view of typical flowers of 'Visinfsalimp'.

DETAILED BOTANICAL DESCRIPTION

The aforementioned photographs and following observations and measurements describe plants grown in Carleton, Mich. during the autumn in a polycarbonate-covered greenhouse and under conditions and practices which approximate those generally used in commercial New Guinea *Impatiens* production. During the production of the plants, day and night temperatures ranged from 18° C. to 24° C. Measurements and numerical values represent averages for typical flowering plants. Single plants were grown in one-gallon containers and had been growing for 17 weeks when the photographs and the detailed description were taken. In the following description, color references are made to The Royal Horticultural Society Colour Chart, 2001 Edition, except where general terms of ordinary dictionary significance are used.

Botanical classification: *Impatiens hawkeri* 'Visinfsalimp'.

Parentage:

*Female, or seed, parent.*—Proprietary selection of *Impatiens hawkeri* identified as code No. 05-511, not patented.

*Male, or pollen parent.*—*Impatiens hawkeri* 'Visinfsal', disclosed in U.S. Plant Pat. No. 16,275.

Propagation:

*Type.*—Vegetative cuttings.

*Time to initiate roots, summer.*—About 14 days at 20° C. to 22° C.

*Time to initiate roots, winter.*—About 18 days at 19° C. to 21° C.

*Time to produce a rooted young plant, summer.*—About 18 days at 20° C. to 22° C.

*Time to produce a rooted young plant, winter.*—About 21 days at 19° C. to 21° C.

*Root description.*—Fibrous, medium in thickness; white in color.

*Rooting habit.*—Freely branching; moderately dense.

Plant description:

*Plant form.*—Compact, upright, outwardly spreading and mounded plant habit.

*Growth and branching habit.*—Vigorous and freely branching habit; about ten lateral branches developing at the base; dense and bushy growth habit; pinching, that is, removal of the terminal apices, is typically not required, but will enhance branching.

*Plant height.*—About 25 cm.

*Plant diameter or spread.*—About 44 cm.

*Lateral branches.*—Length: About 23.5 cm. Diameter: About 9 mm. Internode length: About 4.2 cm. Texture: Smooth, glabrous. Color: Close to 183A.

Foliage description:

*Arrangement.*—Opposite or in whorls, simple.

*Length.*—About 12.8 cm.

*Width.*—About 3.5 cm.

*Shape.*—Elliptical.

*Apex.*—Acuminate.

*Base.*—Attenuate.

*Margin.*—Serrulate with ciliation.

*Texture, upper and lower surfaces.*—Smooth, glabrous.

*Venation pattern.*—Pinnate.

*Color.*—Developing leaves, upper surface: Close to 147A. Developing leaves, lower surface: Close to 148A. Fully expanded leaves, upper surface: Darker than 147A; venation, close to 187C. Fully expanded leaves, lower surface: More grey than 187B; venation, close to 187B.

*Petiole.*—Length: About 1.5 cm to 2 cm. Diameter: About 3 mm. Texture, upper and lower surfaces: Smooth, glabrous. Color, upper and lower surfaces: Close to 187C.

Flower description:

*Flower type and flowering habit.*—Single axillary flowers; freely flowering habit; usually about six to seven flowers and flower buds per lateral branch; flowers positioned above the foliage and typically face upright to outwardly.

*Flower longevity.*—Flowers last about one week under greenhouse conditions; petals self-cleaning, gynoecium persistent.

*Fragrance.*—Not detected.

*Natural flowering season.*—Year-round under greenhouse conditions; in the garden, flowering from spring until fall in California; plants begin flowering about six to eight weeks after planting.

*Flower size.*—Diameter: About 7.8 cm by 7.8 cm. Depth: About 3.2 cm.

*Flower buds.*—Length: About 2.5 cm. Diameter: About 1.5 cm. Shape: Ovoid; pointed. Color: Close to 52A.

*Petals.*—Quantity/arrangement: Five per flower in a single whorl. Length, banner petal: About 3.7 cm. Length, lateral petals: About 4 cm. Length, lower petals: About 3.8 cm. Width, banner petal: About 6 cm. Width, lateral petals: About 5.1 cm. Width, lower petals: About 5.3 cm. Shape: Cordate. Apex: Emarginate to cordate. Base: Acute. Margin: Entire. Texture, upper and lower surfaces: Smooth, glabrous; velvety. Color: When opening, upper surface: Close to 50A. When opening, lower surface: Close to 58C. Fully opened, upper surface: Close to 52B; towards the margins and apex, close to 52A; towards the base, close to 75C to 75D; at the base, close to N66A; color does not fade with development. Fully opened, lower surface: Close to 55B.

*Sepals.*—Quantity/arrangement: Three; one modified into an elongated spur. Length: About 1.8 cm. Width: About 6 mm. Shape: Elliptical. Apex: Acuminate. Base: Obtuse. Margin: Entire. Texture, upper and lower surfaces: Smooth, glabrous. Color, upper surface: Close to 197C tinted with close to 182B. Color, lower surface: Close to 183D. Spur length: About 5.5 cm. Spur diameter: At flower, about 3 mm; at apex, less than 1 mm. Spur texture: Smooth, glabrous. Spur color: Close to 186A to 186B.

*Peduncles.*—Length: About 4.6 cm. Diameter: About 2 mm. Angle: About 55° from vertical. Strength: Strong. Texture: Smooth, glabrous. Color: Close to 185A.

*Reproductive organs.*—Stamens: Quantity: Five fused at anthers; filaments free. Anther size: About 3 mm by 6 mm. Anther color: Close to 20C. Pollen amount: Moderate. Pollen color: Close to 11D. Pistils: Quantity per flower: One. Pistil length: About 5 mm. Stigma shape: Rounded. Stigma color: Close to 62D. Style color: Close to 62D. Ovary color: Close to 59A.

*Seed/fruit.*—Seed and fruit production have not been observed.

Disease/pest resistance: Plants of the new *Impatiens* have not been observed to be resistant to pathogens and pests common to New Guinea *Impatiens*.

Temperature tolerance: Plants of the new *Impatiens* have been observed to tolerate temperatures from about 16° C. to about 30° C.

It is claimed:

1. A new and distinct New Guinea *Impatiens* plant named 'Visinfsalimp' as illustrated and described.

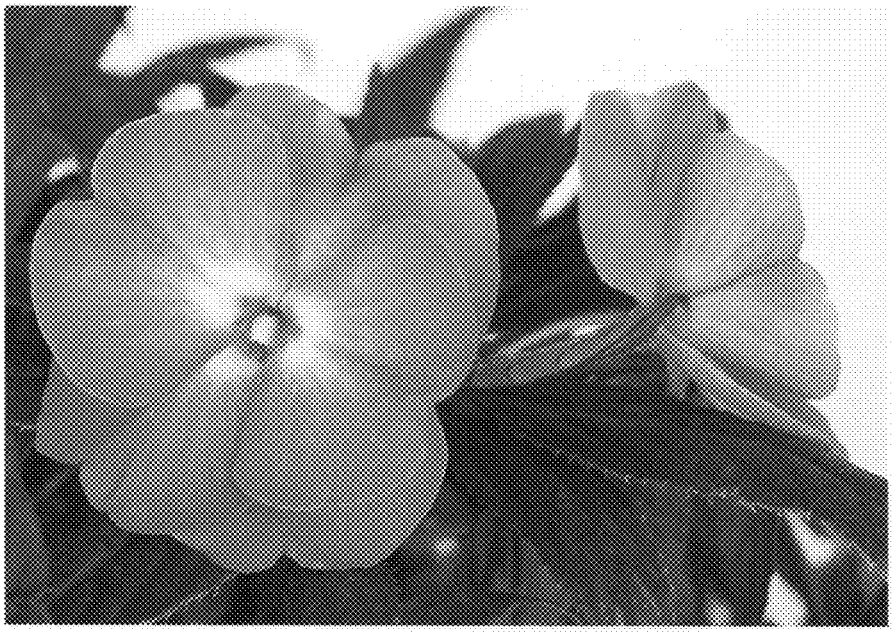
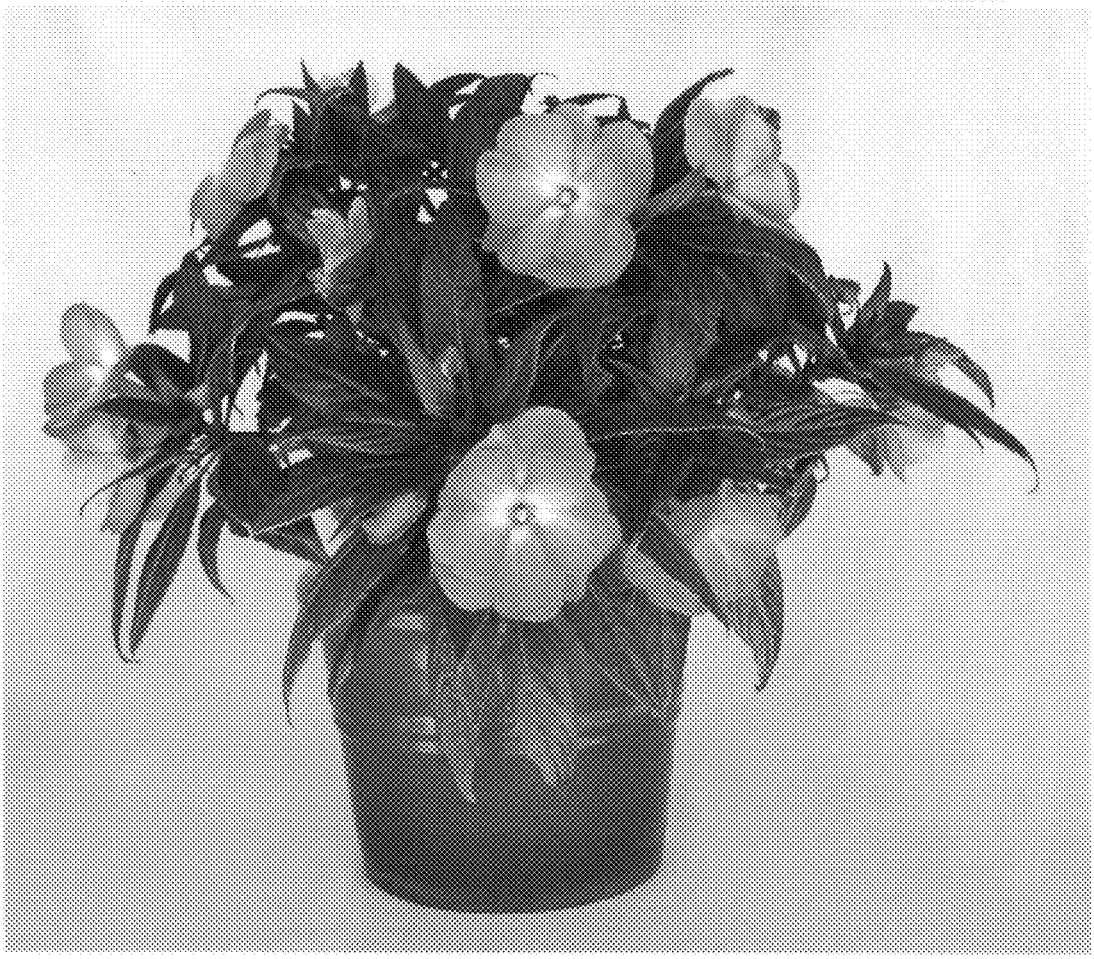

* * * * *